United States Patent [19]

Veech

[11] Patent Number: 5,719,119

[45] Date of Patent: Feb. 17, 1998

[54] PARENTERAL NUTRITION THERAPY WITH AMINO ACIDS

[75] Inventor: Richard L. Veech, Rockville, Md.

[73] Assignee: British Technology Group, Ltd., London, England

[21] Appl. No.: 53,291

[22] Filed: Apr. 26, 1993

Related U.S. Application Data

[63] Continuation of Ser. No. 782,751, Oct. 21, 1991, abandoned, which is a continuation of Ser. No. 479,237, Feb. 12, 1990, abandoned, which is a continuation of Ser. No. 940,332, Dec. 17, 1986, which is a continuation-in-part of Ser. No. 810,916, Dec. 18, 1985, abandoned.

[51] Int. Cl.$^6$ .................................................. A61K 38/00

[52] U.S. Cl. ........................ 514/2; 514/546; 514/557; 514/561; 514/578; 424/601; 424/633; 424/677; 424/678; 424/679; 424/680; 424/719

[58] Field of Search .................................. 424/601, 633, 424/677, 678, 679, 680, 719; 514/561, 557, 578, 546, 2

[56] References Cited

U.S. PATENT DOCUMENTS

| | | | |
|---|---|---|---|
| 4,237,167 | 12/1980 | Cavazza | 514/556 |
| 4,279,917 | 7/1981 | Takami et al. | 514/400 |
| 4,415,556 | 11/1983 | Bretschneider | 424/677 |
| 4,491,589 | 1/1985 | Dell et al. | 514/400 |
| 4,649,050 | 3/1987 | Veech | 424/601 |
| 4,663,166 | 5/1987 | Veech | 424/663 |
| 4,670,261 | 6/1987 | Samejima et al. | 424/600 |
| 5,100,677 | 3/1992 | Veech | 424/677 |

*Primary Examiner*—Kevin E. Weddington
*Attorney, Agent, or Firm*—Hill, Steadman & Simpson

[57] ABSTRACT

Parenteral nutrition aqueous solutions are provided which preferably contain glutamine together with other organic nitrogen containing compounds. The respective concentrations of the compounds present in any given such solution are typically approximately multiples of the concentration of the same compounds as found in normal human plasma, and the respective mole ratios of various such compounds in any given such solution relative to one another are approximately the same mole ratio associated with the same compounds as found in normal human plasma. Processes for using such solutions are provided.

14 Claims, No Drawings

PARENTERAL NUTRITION THERAPY WITH AMINO ACIDS

RELATED APPLICATIONS

This is a continuation of application Ser. No. 782,751, filed Oct. 21, 1991; now abandoned, which is a continuation of application Ser. No. 479,237, filed Feb. 12, 1990 which is now abandoned, which is a continuation of application Ser. No. 940,332, filed Dec. 17, 1986, which is a continuation-in-part of my previous now U.S. patent application Ser. No. 810,916 filed Dec. 18, 1985, now abandoned.

My previously filed U.S. patent application Ser. No. 747,792 (now U.S. Pat. No. 4,663,289), application Ser. No. 747,858 (now U.S. Pat. No. 4,649,050), application Ser. No. 748,232 (now U.S. Pat. No. 4,663,166), and application Ser. No. 748,184 (now U.S. Pat. No. 4,668,400) all filed Jun. 24, 1985 may be considered to be related to my present case.

BACKGROUND OF THE INVENTION

1. Field of the Invention

This invention lies in the field of parenteral nutrition therapy, and especially in the field of amino-acid containing solutions and methods for practicing such therapy.

2. Prior Art

The use of acetate in parenteral fluids developed in the late 40's and early 50's following reports that "acetate could serve as an alternative source of fixed base such as bicarbonate" (Mudge G H, Manning J A, Gilman A. Sodium acetate as a source of fixed base. *Proc Soc Exptl Biol Med* 71:136–138, 1949; Fox C L, Winfield J M, Slobody L B, Swindler C M, Lattimer J K. Electrolyte solution approximating plasma concentrations with increased potassium for routine fluid and electrolyte replacement. *J Am Med Asso* 148: 827–833, 1952), The routine use of acetate in parenteral fluids has grown over the past 40 years to the point where the present commercially available amino acid supplements now contain from 40 to 150 mM acetate (*Facts and Comparisons* March 1984, pp 36–37d. Lippincott, St. Louis) even though the normal level of blood acetate is generally controlled at below 0.2 mM in blood (Bergmeyer H U, Moellering H. Enzymatische besimmung von acetat. *Biochem Z* 344:167–189, 1966).

Acetate was used in parenteral fluids for four major reasons, the first being low cost, and the second, ignorance of its toxic effects. The third was an attempt to avoid hyperchloremic acidosis. Amino acid solutions which included amino acids as their chloride salts lead to hyperchloremic acidosis. The use of acetate as an anion avoided this problem and created a solution which had a pH between 5.5 and 6.5, thus avoiding the precipitation of the divalent cations calcium and magnesium, often included in parenteral fluids. It has generally been assumed that the inorganic pyrophosphate which is formed during the metabolism of acetate is instantly hydrolyzed to 2 inorganic phosphates (Kornberg A. In: *DNA Replication* 1981, pp. 55–56, W H Freeman, San Francisco) by the ubiquitous and highly active inorganic pyrophosphatase (Shatton J B, Shah H, Williams A, "Pyrophosphatase in normal and hepatic tumors of the rat," *Cancer Res.* 41:1866–1872, 1981). This is now known not to be the case (Veech R L, Gitomer W L, King M T, Balaban R S, Costa J L, Eanes E D. "The effects of short chain fatty acid administration on hepatic glucose, phosphate, magnesium and calcium metabolism," In Brautbar N, ed., *Myocardial Bioenergentics and Compartmentation*, New York, Raven Press, 1986, pp. 617–646). Administration of unphysiological levels of acetate causes a 200 fold increase in hepatic inorganic pyrophosphate, a five fold increase in total liver calcium, and a doubling of total metabolizable liver phosphate within 5 minutes of administration. This massive increase in liver calcium, phosphate and pyrophosphate means that, in the rat, the entire blood content of calcium must be removed 4 times to provide this increase. This store can only come from bone destruction. This is the cause of the chronic bone pain and metabolic bone disease seen in patients on current amino acid parenteral nutrient supplements. (See *Facts and Comparisons* pp. 35f, J. B. Lippincott, St. Louis, 1984.)

The fourth reason acetate was included in the amino acid mixtures, particularly those containing sulfur, was to avoid a metabolic acidosis. By adding acetate to the mixture, an alkalizing agent was administered, which, at the time, was thought to be harmless. This has now been proven not to have been the case. The improvement here consists in substituting for acetate other anionic metabolites which may accomplish this function in a non-harmful manner.

Another adverse consequence of the use of acetate in parenteral nutrition fluids is the lowering of the phosphorylation potential which occurs in tissues exposed to high levels of acetate (Veech, R L et al, 1986). This inevitably results in an increased $O_2$ demand for any organ to do a comparable amount of work. In short, this decreases the metabolic efficiency of the organism because less energy is released from each ATP utilized.

Another well known and undesirable consequence of the use of acetate is the release of adenosine from tissues. (Laing C-S, Lowenstein J M, Metabolic control of the circulation, effects of acetate and pyruvate. *J Clin Invest* 62:1029–1038, 1978). Adenosine is a potent vasodilator. Given the well known occurrence of hypotension (Graefe U et al, Less dialysis induced morbidity and vascular instability with bicarbonate in dialysate. *Ann Intern Med* 88: 332–336, 1978) during dialysis where 35 to 45 mM acetate is used, the not uncommon occurrence of hypotension and nausea sometimes seen during the administration of parenteral nutrition solutions may be related to adenosine release which can be avoided by the choice of a different anion than acetate in the formulation.

Finally, the profound lethargy and weakness experienced by patients for up to 2 days following acetate hemodialysis is not dissimilar clinically from the weakness complained of by patients receiving parenteral nutrition. It is not unreasonable to expect that elevated muscle $Ca^{2+}$ plays a role in the functional myopathy seen in both of these clinical situations.

Many current parenteral fluids marketed in the U.S. at present use, in their formulations, a racemic mixture of d,l-lactate. Because of the recognized dangers inherent in giving large volumes of normal saline to patients whose renal excretory capacity is often compromised, Ringer's lactate is the most common complex electrolyte fluid parenterally given in this country today. It was originally formulated because of the hyperchloremic acidosis which resulted from treating children with infantile diarrhea with normal saline (Hartmann A F, The theory and practice of parenteral fluid administration. *J Am Med Asso* 103:1349–1354, 1934). It is now recognized that much lower levels than the 14 mM d-lactate present in Ringer's lactate solution can have obvious untoward effects (Oh M S et al D-Lactic acidosis in a man with short bowel syndrome. *N Eng J Med* 301:249–251, 1979). What is not recognized widely is that d-lactate, while being metabolized only slowly by the body, nevertheless is readily transported into cells by the monocarboxylate carrier present on the plasma membranes of most cells (Olendorf W H, Blood brain barrier permeability to lactate. *Eur J Neurol* 6:49–55, 1971). The result is that not only d-lactate, but also an equivalent amount of $K^+$ are transported into tissues, thereby increasing their osmotic burden. In some cases, this increase can significantly contribute to the so called "idiogenic osmoles" which can be fatal during the treatment of diabetic ketoacidosis with alkalinizing agents such as d,l-lactate. There seems no adequate rationale for the inclusion of d,l-lactate in parenteral fluids any longer. The alternative use of l-lactate, while preferable to the presently used d,l-lactate, is likewise not an optimum alternative to the use of acetate.

In addition to the inappropriate use of acetate, the prior art amino acid formulations suffer because they are commonly derived from the amino acid composition of casein, a common milk protein, and bear little resemblance to the normal human plasma concentrations of free amino acids. Certain classes of amino acids are even missing, particularly the major plasma amino acid, glutamine, which is essential to the function of many organs, such as kidney and gut. It is further known that the plasma concentrations of amino acids are carefully regulated. It is, therefore, desirable that the prior art compositions be replaced by mixtures wherein the respective amino acid concentrations, relative one to another, resemble the plasma to which such are being added.

Finally, the hormonal balance in many patients receiving such treatments favors the breakdown of protein with concurrent loss of muscle and tissue mass and the synthesis of glucose and urea. The action of hormones cab be effected by control of the redox state (Sistare F D, Haynes R D, *J Biol Chem* 260:12748–12753, 1985).

Present parenteral nutritional supplements in malnourished patients generally fail either to restore positive nitrogen balance, or to achieve a demonstrable increase in functional capacity when administered, for example, over a one week period.

The common conventional parenteral amino acid supplements currently in use are listed in Table 1 (below). It is clear from the Table that the current parenteral formulations in no way resemble the amino acid compositions seen in normal plasma.

Attempts have been made to develop amino acid formulations based on the normal amino acid compositions present in postprandial samples from blood (see U.S. Pat. No. 4,491,589, Dill R B, Waters R W, Hurd W C. Amino acid solutions for parenteral nutrition and methods of formulation and use). However, these attempts fail to address the acidosis resulting from the metabolism of amino acids and neither do they make any attempt to define the non-amino acid anionic components in such mixtures so as to prevent the development of bone pain and metabolic disease which accompanies such therapy. Further, the ratio scheme of purported non-essential to essential amino acids may not meet the various clinical situations requiring such therapy.

The "essential" amino acids listed by Dell et al. U.S. Pat. No. 4,491,589 are 11 in number whereas the "essential" groups listed in *Fact and Comparisons* are only 8, Omitting l-histidine, l-cysteine, and l-tyrosine. The essential nature of l-histidine in man is not universally agreed to. Further, most authorities would agree that if l-phenylalanine is given, then its hydroxylation product l-tyrosine is not "essential".

TABLE 1

Composition of Commercial Parenteral Nutrition Fluids Values are given in millimoles/Liters (mMol/l). The values are taken from Facts and Comparisons March 1984, pp 35d-37d, Lippincott, St. Louis.

| Component | Normal Plasma | Aminosyn 3.5% Abbott | Travasol 5.5% Travenol | FreeAmine 6.9% McGaw | Hepamine 9% McGaw |
|---|---|---|---|---|---|
| Essential | | | | | |
| l-Ile | 0.036 | 19.2 | 20.1 | 58.0 | 68.7 |
| l-Leu | 0.076 | 25.1 | 26.0 | 105.0 | 84.0 |
| l-Lys$^+$ | 0.106 | 17.2 | 21.8 | 28.1 | 41.8 |
| l-Met | 0.03 | 9.4 | 21.3 | 16.8 | 6.7 |
| l-Phe | 0.029 | 9.3 | 20.6 | 19.4 | 6.1 |
| l-Thr | 0.082 | 15.3 | 19.3 | 16.8 | 37.8 |
| l-Trp | 0.054 | 2.75 | 4.85 | 4.4 | 3.2 |
| l-Val | 0.136 | 23.9 | 21.5 | 75.2 | 71.8 |
| Non-Essential | | | | | |
| l-Cyst** | 0.24 | — | — | — | — |
| l-Ala | 0.142 | 50.3 | 128.0 | 44.9 | 86.5 |
| l-Arg$^+$ | 0.041 | 19.7 | 32.8 | 33.3 | 34.5 |
| l-Asp$^-$ | 0.02 | — | — | — | — |
| l-Asn | 0.02 | | | | |
| l-Glu$^-$ | 0.031 | | | | |
| l-Gln | 0.300 | — | — | — | — |
| Gly | 0.124 | 59.7 | 152.0 | 44 | 120.0 |
| l-His | 0.051 | 6.77 | 15.5 | 10.3 | 15.5 |
| l-Pro | 0.105 | 26.1 | 20.0 | 54.8 | 69.6 |
| l-Ser | 0.081 | 14 | — | 31.4 | 47.6 |
| l-Tyr | 0.030 | 1.71 | 1.22 | — | — |
| Other N Compounds | | | | | |
| l-Carnitine | 0.047 | — | — | — | — |
| l-Citrulline | 0.019 | — | — | — | — |

TABLE 1-continued

Composition of Commercial Parenteral Nutrition Fluids
Values are given in millimoles/Liters (mMol/l). The
values are taken from Facts and Comparisons March 1984, pp
35d-37d, Lippincott, St. Louis.

| Component | Normal Plasma | Aminosyn 3.5% Abbott | Travasol 5.5% Travenol | FreeAmine 6.9% McGaw | Hepamine 9% McGaw |
|---|---|---|---|---|---|
| 1-Ornithine | 0.033 | | | | |
| Electrolytes mEq/L | | | | | |
| $Na^+$ | 163–145 | 7 | 47* | 3 | 70* | 10 | 10 |
| $K^+$ | 3.5–5.0 | — | 13 | — | 60 | — | — |
| $Mg^{2+}$ | –.53 | — | 3 | — | 10 | — | — |
| $Cl^-$ | 100–106 | — | 40 | — | 70 | 3 | 3 |
| Acetate | 0.02 | 46 | 58 | 48 | 102 | 57 | 62 |
| 1-lactate$^-$ | 0.6–6 | — | — | — | — | — | — |
| pyruvate$^-$ | 0.1–1 | — | — | — | — | — | — |
| Pi mM/L | 1–1.45 | — | 3.5 | — | 30 | — | 10 |
| $S_2O_4^{2-}$ | 0 | 0.5 | 0.5 | — | — | — | — |
| $HSO_3$ | 0 | 0 | 0 | 3 | 3 | 3 | 3 |
| Glucose | 3.9–5.6 | | | | | | |
| mOsm/L | 311 | 357 | 447 | 581 | 850 | 620 | 785 |

*Formulation with added electrolytes.
**Sulfur containing amino acids contents of human plasma from Felig P, Owen OE, Wahren J, Cahill GF, J Clin Invest 48:584-594, 1969.

BRIEF SUMMARY OF THE INVENTION

This invention provides a new class of formulations of nitrogen containing parenteral nutrition fluids which overcomes the prior art deficiencies above referenced, which contain the major plasma amino acids, which avoid the toxicity of acetate and other prior art components, and which optimally may achieve normalized redox balance within the organs of mammals to which such are administered (thereby to control and normalize the cellular phosphorylation state). The invention further provides methods for accomplishing nutrition therapy using such formulations.

More particularly, this invention is directed in one aspect to a new and improved class of non-hyperchloremic, alkalinizing, compositions which prevent both metabolic acidosis and metabolic bone disease. Such compositions comprise water having dissolved therein:

(A) from about 1 to 150 mMoles/Liter of each of at least one of the metabolizable nitrogen containing compounds appearing in Table 5 below with the total quantity of such compounds in any given such composition being not more than about 1000 mMoles/L (and preferably from about 50 to 800 mM);

(B) from about 0.1 to 150 mMoles/L of at least one carboxylic metabolite anion selected from the group consisting of 1-lactate, pyruvate, d-beta-hydroxybutyrate, acetoacetate, alphaketoglutarate and bicarbonate;

(C) from about 0.1 to 150 mM/L of at least one cation selected from the group consisting of sodium, potassium, calcium, magnesium, and ammonium.

The notation "mMoles/L" as used herein has conventional reference to millimoles per liter (sometimes shown as mM/l or the like).

Optionally and additionally such a composition can contain at least one osmotically active nonionic water soluble nutrient, such as glucose, in a total quantity ranging from about 5 to 400 mMoles/L.

Also, optionally, the solution may contain added electrolytes as defined in (C) above as accomplished in the prior art amino acid solutions (see Table 1).

In another aspect this invention is directed to an improved in vivo process for accomplishing parenteral nutrition which comprises introducing intravenously into a human being a composition from the class above described preferably at a rate which is sufficient to be nutritionally effective. Such a rate with such a composition can also be generally effective in normalizing organ function particularly when near equilibrium couples are employed as taught hereinbelow.

These new parenteral organic nitrogen containing fluids avoid the toxic effects of the current commercially available 40 to 140 mM acetate containing parenteral nutrition solutions which lead to pathological accumulations of calcium, phosphate, and inorganic pyrophosphate within liver and other organs, and which result in the chronic bone pain and metabolic bone disease seen in patients with long term parenteral nutrition.

Optionally, a composition from the class above described may additionally contain dissolved therein glutamine. Preferably, the quantity of glutamine employed in any given such composition is as herein below described.

The glutamine containing compositions of the present invention are applicable for use in various particular parenteral fluid therapy applications. The concentrations and the relationship of the component concentrations to one another in such application can be varied. In use, a glutamine containing composition may result in an increase in organ protein content and/or an increase in organ functional capacity compared to compositions of the class above described.

Preferably, in the compositions of this invention, the anions above indicated are employed in the form of pairs which correspond to near-equilibrium couples in accord with the following table:

TABLE 2

Carboxylate Near Equilibrium Couples

| Anion Couple | mEq ratio |
| --- | --- |
| l-lactate⁻/pyruvate⁻ | 1:1 to 20:1 |
| d-betahydroxybutyrate⁻/acetoacetate⁻ | 0.5:1 to 6:1 |
| bicarbonate⁻/$CO_2$ | 1:1 to 100:1 |

Preferably, also, a composition of this invention contains at least 5 of such nitrogen containing compounds of Table 5, more preferably at least 10, still more preferably at least 15, and most preferable all of the compounds of Table 5. Preferably, when more than one such compound is present, the relative quantities of each in relation to the other(s) thereof present follows the hierarchical listing order shown in Table 5.

An object of the present invention is to provide parenteral nutritional compositions which do not contain toxic levels of acetate or d,l-lactate.

Another object is to provide parenteral nutritional compositions which contain at least one l-amino acid and at least one monocarboxylic anionic metabolite.

Another object is to provide therapeutic organic nitrogen containing fluid compositions which include near equilibrium couples which comprise either metabolite carboxylic anions or amino acids.

Another object is to provide a class of organic nitrogen containing parenteral nutrition fluids which, when administered, regulate and control the cellular phosphorylation state, thus normalizing and improving the efficiency of organ function in a living mammal.

Another object is to provide a class of mixtures of organic nitrogen containing compounds which mixtures are adopted to be employed, if desired, in multiples of the physiologic concentrations of such compounds found in normal human plasma and which mixtures are not simple compositions derived from the amino acid content of casein or other low cost hydrolyzable proteins.

Another object is to provide aqueous compositions containing amino acids and certain redox action carboxylic acid near equilibrium couples which are suitable for use in parenteral nutrition therapy to restore and maintain muscle and other cellular functions.

Other and further objects, aims, purposes, features, advantages, embodiments, applications and the like will be apparent to those skilled in the art from the teachings of the present specification taken with the claims.

DETAILED DESCRIPTION

Loss of organ protein and mass, with the conversion of the constituent amino acids to glucose, acetyl CoA, and urea, is a normal consequence of starvation or malnutrition. This process, called negative nitrogen balance, is accelerated by trauma, burns or wounds, infections and malignancy, and by surgery. It is recognized that the morbidity and mortality associated with surgery or cancer chemotherapy can be decreased if seriously ill patients can be returned toward a nutritionally normal state prior to surgery, or can be maintained in such a state while in the postoperative period or while undergoing a chemotherapy. Currently, therefore, parenteral nitrogen infusions are used to treat negative nitrogen balance when (1) the alimentary tract, by oral, gastrostomy or jujunostomy cannot be used; (2) gastrointestinal absorption of protein is impaired by obstruction, inflammatory disease or complications of antineoplastic therapy; (3) bowel rest is needed because of GI surgery or its complications, such as ileus, fistulae or anastomotic leaks; or (5) burns, trauma, infections, or other such so called hypermetabolic states exist.

It was originally supposed that, if the urinary losses of nitrogen accompanying these states of excessive catabolism could be replaced by the intravenous administration of nitrogen containing compounds in the form of amino acids in conjunction with carbohydrates such as glucose, or alternatively fat emulsions, then protein wasting could be reversed. While this is theoretically true, in practice this often proves not to be the case. It is now documented that, in spite of the provision of up to 1.5 g/kg of parenteral nitrogen/day for about one month pre-operatively, there is often no measurable increase in total body nitrogen. This naturally raises questions, not only about the hormonal status of such patients, but also about the adequacy of the specific amino acid formulations that are being administered, and whether the present formulations take advantage of newer information concerning the metabolic factors responsible for control of the rates of protein synthesis and degradation. Recent work now indicates that the current forms of parenteral nutrition fluids, to which high levels of acetate are routinely added as a method to insure the solubility of the constituents of the solution and to avoid the complication of hyperchloremic acidosis which were present in the early formulations which included amino acids as their chloride salts, themselves result in a number of toxic side effects, such as hyperglycemia, chronic bone pain, metabolic bone disease, and also a functional myopathy characterized as weakness of effort which results from the use of acetate. These undesired side effects may be ameliorated, or avoided altogether, when the acetate used in the prior art formulations is replaced by other more physiologically normal constituents as taught herein. There is further evidence to suggest that the specific concentrations and components of the nitrogenous compounds present in the current commercial formulations are not optimized so as to promote a positive nitrogen balance and a return to physiologically normal status. For these reasons, the present and new improved formulations of parenteral amino acid supplements have been created as taught herein.

These compositions provide less toxic and more efficacious forms of parenteral nitrogenous nutritional supplements to treat patients in negative nitrogen balance for the above listed reasons.

The proper alternative to the use of acetate and/or d,l-lactate in nutritional nitrogen containing parenteral fluids, is the inclusion of a balanced ratio of redox active carboxylic acid near equilibrium anion couples, as taught herein. While control of pH is widely recognized as important in parenteral fluid therapy, the importance of the control of the redox states in such fluids has not generally been appreciated in clinical practice. While the serious and usually fatal nature of lactic acidosis is recognized, and measurement of the blood lactate/pyruvate ratio in various disease states has been accomplished for many years (Huckabee W E, Relationships of lactate and pyruvate during anaerobic metabolism, *J Clin Invest* 37:244–254, 1957), no previous clinical attempts to use the control of this fundamental cellular property of the redox states as a therapeutic tool are now known. The cellular levels of many metabolites, including many crucial amino acids, are functions of the intracellular redox states (Krebs H A, Veech R L. The energy level and metabolic control in mitochondria, pp. 329–384, *Adriatica Editrica*, Bari, 1969). Thus, the concentration of the central amino acid transaminase pairs, namely alpha ketoglutarate x glutamate, and oxaloacetate x aspartate, or pyruvate x alanine, as well as the ketoacids of the branched chain amino acids, ketoisovaleric, and ketoisocaproic, are related to the redox state of one or another of the cellular redox states as the result of highly active transaminase systems which maintain a state of near equilibrium between the various cellular components. Administration of solutions of amino acids alone, without simultaneous administration of one or another substrate couple with which that amino acid is in a state of near equilibrium, results in a change of the general cellular redox state towards that state which is characteristic of the starved state. During starvation, characterized by a general reduction of all the cellular redox states, or $[NA(P)D^+]/[NAD(P)H]$ ratios, there is a breakdown of protein into amino acids and an increase in gluconeogenesis. This is precisely the situation which parenteral nutrition with amino acids is trying to reverse. The same situation of reduction of cellular redox states occurs under the influence of catabolic hormones, such as glucagon, sympathomimetic agents, and steroids. The present class of formulations, therefore, may be used to insure that the cellular redox state of the cells in a living mammal during parenteral nutrition achieves a level characteristic of the fed state when protein synthesis generally exceeds the rate of protein breakdown.

A second factor of major importance bearing upon the control of the redox state is that the cytoplasmic $[NAD^+]/[NADH]$ is directly related to the major cellular energy level, or to the cytoplasmic phosphorylation state of $[ATP]/[ADP]\times[Pi]$ ratios through the action of the glyceraldehyde 3 phosphate dehydrogenase reaction and the 3 phosphoglycerate kinase reactions (Veech R L, Lawson J W R, Cornell N W, Krebs H A. The cytoplasmic phosphorylation potential. *J Biol Chem* 254:6538–6547, 1979). Control of the cytoplasmic phosphorylation potential allows one to manipulate, within limits, the cellular energy level which determines the degree of efficiency at which any organ operates. It has recently been shown, for example, that the maximum rate at which isolated hepatocytes are able to convert lactate to glucose is at the physiological redox state represented when the [lactate]/[pyruvate] ratio in the bathing media is 10:1 (Sistare F D, Haynes R C, *J Biol Chem* 260:12748–12753, 1985). The same paper shows that, for any class of hormone tested, whether acting through cyclic AMP, through changes on intracellular $Ca^{2+}$, or directly on a receptor and then on nuclear synthesis such as steroids, there is a particular redox state which will allow, or not allow, as the case may be, the hormone class members to maximally express their action. By changing the ratio of redox active metabolite pairs during parenteral fluid therapy, the physician is offered the opportunity to directly alter the redox state of the tissues during such parenteral fluid therapy so as to best achieve the result desired in a particular situation. Thus, in most clinical conditions, such as following trauma, burns or surgery, the hormonal status of the patient favors the catabolism of protein and the making of glucose. While the prevention of the secretion of catabolic hormones in such a situation cannot be prevented, by alteration of the redox state of the parenteral fluids, the effects of these hormonal changes may be modified.

By far the bulk of the protein eaten in the diet is broken down in the gut endothelium to the constituent amino acids. These amino acids are transported in the portal vein to the liver, where they are mainly broken down into urea and glucose (Krebs H A. Some aspects of the energy transformation in living matter. *Brit Med Bull* 9:97, 1953). The amino acid composition of each of the blood, plasma, and extracellular fluid is tightly controlled by the liver, interacting with the muscles and the gut. Depending upon the tissue in question, gradients of from one to almost 100 fold in amino acid concentration between extracellular and intracellular amino acids can build up between blood and tissue in some, but not all, amino acids.

In Table 3 (below) are given the amino acid concentrations in rat and human serum, and in liver as a representative tissue. Also included as a point of reference is the amino acid composition of the ubiquitous intracellular protein, actin, which has a molecular weight of 42,056 with 337 amino acid and amide residues. The values are given as if 1 mole of actin were hydrolyzed completely in 1 liter of intracellular water, since 1 mM is about the concentration of this protein in muscle.

As will be apparent (see Table 1 above), not only do the relative amounts of the various amino acids included in current parenteral nitrogen supplements vary from the physiologically normal distribution, but also important omissions of whole classes of nitrogen containing compounds occur characteristically in the present fluids. Simply to give "nitrogen" in an unphysiological mixture as amino acids whose concentration ratios, one to another, bear no relationship to the normal levels of such amino acids in plasma, is simply to stimulate urea synthesis. Such does nothing to increase the rate of protein synthesis, inhibit the rate of protein breakdown, correct the observed physiological myopathy, or inhibit the action of catabolic hormones which are usually present in excess in situations of trauma, malignancy, or simply malnutrition itself. The provision of adequate glucose to maintain cerebral function at all costs is an evolutionary imperative. The contemporary (prior art) compositions of parenteral nitrogen containing nutritional fluids do nothing to address these fundamental organizational imperatives.

TABLE 3

Amino Acid and Amide Composition of Plasma, Perfused Liver, and a Representative Protein Values are given in mmoles/liter water. The values for rat serum are taken from Lunn PG, Whitehead RG, Baker BA, Br J Nutr 36: 219–230, 1976; for normal human plasma from Guanda OM, Aoki T, Soldner H, Cahill FG. J Clin Invest 57: 1403–1411, 1976. Liver values from perfused rat liver containing normal amino acid levels in a perfusate composed of Krebs-Henseleit are taken from Poso AR, Mortimore GE, Proc Nat'l Acad Sci USA 81: 4270–4274, 1984.

| Amino Acid | MW | Normal Human[4] Plasma | Normal Rat[4] Plasma | Perfused Rat Liver Content | Liver Perfusate Gradient | Actin 1 mMol/ 1L |
|---|---|---|---|---|---|---|
| Essential | | | | | | |
| 1 1-Isoleucine | 131 | 0.036 | 0.114 | | | 30 |
| 2 1-Leucine | 131 | 0.076 | 0.204 | 0.356 | 1.7 | 26 |
| 3 1-Lysine+ | 146 | 0.106 | 0.408 | | | 19 |
| 4 1-Methionine | 149 | 0.03 | 0.060 | 0.114 | 1.9 | 17 |
| 5 1-Phenylalanine | 165 | 0.029 | 0.096 | 0.074 | 0.8 | 12 |
| 6 1-Threonine | 119 | 0.082 | 0.329 | | | 27 |
| 7 1-Tryptophane[1] | 204 | 0.054 | ND | | | 4 |
| 8 1-Valine | 117 | 0.136 | 0.250 | | | 21 |
| Non-Essential | | | | | | |
| 1 1-Alanine | 89 | 0.142 | 0.475 | 2.19 | 4.6 | 29 |
| 2 1-Arginine+ | 174 | 0.041 | 0.220 | 0.04[3] | | 18 |
| 3 1-Aspartate− | 133 | 0.02 | 0.053 | 4.97 | 93.8 | 22 |
| 4 1-Asparagine | 132 | 0.02 | ND | | | 12 |
| 5 1-Cysteine | 121 | 0.24 | 0.034 | | | 6 |
| 6 1-Glutamate− | 147 | 0.031 | 0.158 | 9.19 | 58.2 | 28 |
| 7 1-Glutamine | 146 | 0.300 | ND | 9.18 | | 11 |
| 8 Glycine | 75 | 0.124 | 0.370 | 5.09 | 13.7 | 28 |
| 9 1-Histidine | 155 | 0.051 | 0.092 | 0.836 | 9.1 | 9 |
| 10 1-Proline | 115 | 0.105 | 0.437 | 0.161 | 0.37 | 19 |
| 11 1-Serine | 105 | 0.081 | 0.657 | | | 23 |
| 12 1-Tyrosine | 181 | 0.030 | 0.098 | 0.106 | 1.1 | 16 |
| Other N Compounds | | | | | | |
| $NH_4^+$ | 18 | 0.05 | 0.02 | 0.71 | 35 | |
| 1-ᵞAminobutyrate | 103 | 0.016 | | | | |
| 1-Carnitine[2] | 161 | 0.047 | | 2–4 | 50 | |
| 1-Citrulline | 175 | 0.019 | | 0.050[3] | | |
| 1-Ornithine | 132 | 0.033 | | 0.150[3] | 50 | |
| 1-Taurine | 125 | 0.024 | | | | |

[1]Denckla WD, Dewey HK. The determination of tryptophane in plasma, liver and urine. J Lab Clin Med 69:160–169, 1967.
[2]Rudman D, Ansley JD, Sewell CW, in Carnitine Biosynthesis, Metabolism, and Functions pp. 307–321. Academic Press, 1980.
[3]Raijman L, in The Urea Cycle pp. 243–254, John Wiley, 1976.
[4]The values in this column are based upon the best information now known to the inventor; further study and evaluation may lead to slightly different values.

Table 3 shows the amino acid composition of normal human plasma and the amino acid composition of a normal intracellular protein, actin. It can readily be seen that the composition of plasma is very different from the amino acid composition of a protein. Plasma levels of amino acids often bear little relation to tissue concentrations. Table 2 further illustrates that the amino acid composition of plasma is approximately the same as the amino acid composition of liver for certain amino acids, such as the branched chain amino acids, valine, leucine, and isoleucine, the aromatic amino acids, phenylalanine and tyrosine, and the sulfur containing amino acid, methionine. In contrast, the liver/plasma gradient of other amino acids, particularly those which take place in near-equilibrium, redox-related reactions, such as alanine, glutamate− and aspartate²−, may show concentration gradients from 5 to 100 between perfusing fluid and liver. The same large concentration gradients occur in the case of glutamine. In general, the major traffic in nitrogen between the various organs is borne by alanine, glutamine, and the branched chain amino acids, leucine, isoleucine and valine.

In a 70 kg normal man, the major repository of the 6 kg of nitrogen is the tissue proteins, while the free tissue amino acid pools comprise less than 1% of the total amino acids. Tissue protein is in a dynamic state with half lives ranging from less than one hour to weeks, and with the overall turnover being about 300 g/day in a 70 kg man.

Protein synthesis obviously requires a supply of amino acids. In addition, it requires that the gradients of amino acids between extracellular fluid and cells remain normal. The latter function of the cell is the result of a variety of active, energy-requiring uptake systems, which, in turn, demand that the cellular energy state, or $[ATP]/[ADP] \times [Pi]$, and its related redox state, or $[NAD^+]/[NADH]$, are normal. In fact, by far the major fate of ingested amino acids is not for the synthesis of protein, but rather to serve either as substrates for gluconeogenesis, or as precursors of acetyl CoA for combustion in the Krebs cycle. Most of the nitrogen of ingested proteins, and their hydrolyzed amino acids, therefor, end as urea. The carbon skeletons end as either glucose, or as ketone bodies, being metabolized by the various transaminase reactions with glutamate, or forming one or another forms of CoA, with or without an intermediate form of an acyl carnitine.

In trauma (Kinney J M. The metabolic response of injury. in *Nutritional aspects of care in the critically ill*, Richards J R, Kinney J M, eds. pp 95–133, Churchill Livingston, 1977), in malnutrition, and in many malignant states, the degradative reactions of proteins are accelerated over synthesis, with excessive catabolism of the released amino acids to glucose, ketone bodies, and urea. The result is that the patient shows negative nitrogen balance and muscle wasting. Attempts have been made using so called parenteral nutrition solutions of amino acids to reverse this degradation of muscle and other organ mass. Unfortunately, using conventional forms of parenteral amino acid formulations, no significant gain in muscle nitrogen can be seen in the first weeks or months of therapy (Yeung C K et al. Effect of an elemental-diet on body composition. A comparison with intravenous nutrition. *Gastroenterology* 77:652–657, 1979).

A first possibility or mode for improvement is the development of alternative formulations of nitrogen compound containing parenteral nutrient formulation which avoid the use of 40 to 150 mM acetate in all current amino acid containing parenteral nutrition formulation, (*Facts and Comparisons* March, 1984, pp. 36a–37d, J B Lippincott, St. Louis) so as to avoid the chronic bone pain, the metabolic bone disease, and the profound disordering of calcium, phosphate and pyrophosphate homeostasis which accompany the current use of unphysiological levels of acetate in parenteral nutrition formulations. Instead of acetate, at least one carboxylic metabolite, or more preferably, at least one redox balanced mixture as shown in Table 2 containing the near equilibrium carboxylic acid couples l-lactate/pyruvate, d-betahydroxybutyrate/acetoacetate, and/or bicarbonate/$CO_2$ are used as substitutes for acetate (see, for example, my copending U.S. patent application Ser. No. 748,232).

Another alternative or mode for improvement is to employ nitrogen containing parenteral nutrient solutions as provided by the present invention wherein the redox state is controllable after administration using certain amino acids themselves, along with the appropriate redox and transaminase partner, when employed in the concentration ratios found in normal healthy animals, or in designed variations of those ratios. Specific effects may be achieved, such as the modification of hormone action as described previously. For example, the normal redox partner of l-lactate is pyruvate, but, in solution, pyruvate tends to form the inactive dimer parapyruvate. This means that it preferably should be added just prior to use, as is now preferably done with cysteine. Such alternatives achieve generally the same desired redox control, but have the practical advantage of a longer shelf life. The use of the other major permeant redox active couple, [d-hydroxybutyrate]/[acetoacetate] also is limited since, in solution and over long periods of time, acetoacetate tends to decarboxylate. This property of acetoacetate means that it, too, must be added just prior to use. It may not be possible to avoid this problem and stay within the constraints imposed by physiological constraints. Nevertheless, certain methods, as taught herein, of achieving redox control are possible, which have the practical advantage of long shelf life.

As aforementioned, the metabolite anions used in the compositions of this invention exert a desirable alkalinizing action which avoids metabolic acidosis and thereby provides alkalinizing action as desired.

Thus, normal plasma contains concentrations of [ammonium$^+$, also characterized herein as $NH_4^+$]× [alphaketoglutarate$^{2-}$]/[glutamate$^-$] the product of which is equivalent to the estimated mitochondrial free [NAD$^+$]/[NADH] ratio (Veech R L, unpublished data) as determined by the intracellular concentration of these metabolites (Williamson, D H, Lund P, Krebs H A, The redox state of free nicotinamide-adenine dinucleotide phosphate in the cytoplasm and mitochondria of rat liver. *Biochem J* 115:609–619, 1967). The stability of alphaketoglutarate is somewhat greater in solution than that of either pyruvate or acetoacetate, depending upon the conditions. Even though large gradients of each of these compounds exist across plasma membranes, and their concentrations in plasma are very low relative to their intracellular concentrations, controlled transport of all of these substrates does occur. If fluids not containing these substrates are given, then the cells alter their metabolism so as to make the infused material contain a predetermined concentration gradient. Addition, therefore, of alphaketoglutarate and $NH_4^+$ in an amino acid solution containing glutamate can control the redox state of the mitochondria.

Another example is the use of various ratios, around the physiologically normal, of [ketoglutarate]/[glutamine] which avoid the use of free ammonia, but which generate the ammonia and the production of intracellular glutamate.

Finally, the glutamate-pyruvate-transaminase reaction makes it possible to control redox state in an amino acid containing parenteral solution using the ratio of [l-alanine]/[l-lactate]. This appears to be useful in situations where the limited shelf life of ketoacids, such as pyruvate, in solution, may call for premixed redox balanced solutions with a long stability. Using a combination of [l-alanine]/[l-lactate] in conditions where this solution stability is needed, and the extra ammonia resulting from the formation of pyruvate from alanine and its subsequent removal as urea, does not present a problem, make this alternative practically useful in certain settings, such as the treatment of battle casualties or civilian catastrophes.

Suitable amino acid containing couples are shown in Table 4 below:

TABLE 4

| Couple | Ratio Range |
| --- | --- |
| [1-Lactate$^-$]/[1-Alanine] | 2:1 to 25:1 |
| [1-glutamine]/[alpha ketoglutarate$^{2-}$] | 2:1 to 50:1 |
| [1-glutamate$^{1-}$] [NH$_4^+$] [alpha ketoglutarate$^{2-}$] | $1 \times 10^{+3} - 100 \times 10^{+3}$ Molar |

The use of one or more of these various redox couples is optionally employed in a solution of this invention whether or not other nitrogen containing compounds are present (including glutamine) when control of the redox state is desired. Other nitrogen containing components present in normal plasma optionally may also be present in a solution of this invention. These new solutions, when compared to the presently available commercial formulations evaluated, for example, using rats with implanted venous cannulae, both before and after the induction of surgical trauma, demonstrate substantially improved capacity to control the redox state.

As those skilled in the art of amino acids appreciate, it has heretofore been the common practice to prepare such in the form of their hydrochloride salts. Evidently, such salts offer the advantages of reliable preparation of crystalline salts in high yields from aqueous solutions or slurries which are themselves prepared variously by conventional total synthesis methods, by acid hydrolysis of inexpensive proteins from a protein source such as casein, degummed white silk, etc., by microbial conversion, by resolution of racemates to produce l-amino acid etc. Such hydrochloride salts when redissolved in water to prepare l-amino acid therapeutic fluids produce hyperchloremia when administered to a patient. To prevent such hyperchloremia, the prior art solutions remove chloride and substitute acetate with others, but different complications described earlier.

To avoid such complications, it is preferred to prepare l-amino acids for use in the present inventive compositions in the form of salts of at least one of the metabolite anions identified herein.

The parenteral aqueous solutions of the present invention preferably include, as solutes, more than one amino acid. In such preferred solutions this quantitative relationship of individual amino acids one to another is preferably such as to correspond to the quantitative relationship of these same respective amino acids in normal plasma. Each of the component amino acids present in such a mixture is preferably present in an amount which is in excess of the amount present in normal plasma. Thus, such mixtures are preferably multiples of normal plasma levels. Leaving aside the concentration of amino acids in the portal vein, the diurnal variations in the amino acid composition of plasma in the systemic circulation are relatively small (Wurtman R J et al., Daily rhythms in the concentrations of various amino acids in human plasma. *N Eng J Med* 279:171–175, 1969). It is, therefore, striking to note that the amino acid concentrations, relative to one another, which are used in the current commercial amino acid nutritional supplements in clinical use, bear little relationship to the amino acid composition of human plasma (see Table 1). Thus, as shown in Tables 1 and 3, the order of decreasing concentration in normal plasma is roughly: 1 glutamine, 2 cysteine, 3 alanine, 4 valine, 5 glycine, 6 lysine$^+$, 7 proline, 8 threonine, 9 serine, 10 leucine, 11 methionine, 12 tryptophane, 13 histidine, 14 arginine$^+$, 15 isoleucine, 16 glutamate$^-$, 17 tyrosine, 18 phenylalanine, 19 asparagine, 20 aspartate$^-$, as shown in the following Table 5:

TABLE 5

Decreasing Concentration of Organic Nitrogen Materials in Normal Human Plasma

| I.D. No. | Material |
|---|---|
| 1 | l-glutamine |
| 2 | l-cysteine |
| 3 | l-alanine |
| 4 | l-valine |
| 5 | glycine |
| 6 | l-lysine |
| 7 | l-proline |
| 8 | l-threonine |
| 9 | l-serine |
| 10 | l-leucine |
| 11 | l-methionine |
| 12 | l-tryptophane |
| 13 | l-histidine |
| 14 | l-arginine |
| 15 | l-isoleucine |
| 16 | l-glutamate |
| 17 | l-tyrosine |
| 18 | l-phenylalanine |
| 19 | l-asparagine |
| 20 | l-aspartate |

In what is believed to be the most commonly used present commercial formulations, the concentrations are disordered from normal in both order and in concentration range. In, for example, the "Travasol" formulation, the concentrations are, relative to the natural order: 4 glycine, 2 alanine, 13 arginine$^+$, 9 leucine 5 lysine, 3 valine, 10 methionine, 19 phenylalanine, 14 isoleucine, 6 proline, 7 threonine, 12 histidine, 13 tryptophane, 14 tyrosine, with the major amino acid in plasma, l-glutamine being omitted altogether, as are the important redox active amino acids, 15 glutamate$^-$ and 19 aspartate$^-$, and also, inexplicably, 8 serine, a precursor of pyruvate.

Through the transaminase reactions, the tissue concentrations of many amino acids are related to one another through the concentration of common ketoacids, particularly pyruvate and alpha ketoglutarate (see Veech R L and Krebs H A, in *The energy level and metabolic control in mitochondria*, pp. 329–382, Adriatica Editrice, Bari, 1969; Brosnan J T, in *The Urea Cycle*, pp. 443–457, John Wiley, New York, 1976). The intracellular amino acid levels are, therefore, importantly related both to the cytoplasmic [NAD$^+$]/[NADH] ratio, and to the mitochondrial [NAD$^+$]/[NADH] ratio, and also to the concentration of ammonia (Williamson D H, Lund P, Krebs H A, *Biochem J* 103:514–427, 1967). Giving one, but not another component, of a near-equilibrium couple must inevitably lead to a distortion of the intracellular concentrations of a number of metabolites. More importantly, distortion of the cellular redox state leads to changes in the cellular energy level or [ATP]/[ADP]×[Pi] ratio because:

$$K_{G+G} = \frac{3PG}{DHAP} \times \frac{ATP}{ADP \times P_i} \times \frac{NADH \cdot H^+}{NAD^+}$$

(see Veech R L, Cornell N W, Lawson J W R, Krebs H A, *J Biol Chem* 254:6538–6547, 1979). It would, therefore, seem reasonable that, during the administration of parenteral nutrition, supplements aimed at restoring muscle function and increasing in protein mass, some consideration be given to control the natural order of metabolite levels, in addition to taking steps to control the cellular redox state and the phosphorylation potential. The mere presentation of nitrogen containing compounds to the body in disordered amounts derived from the composition of hydrolyzed casein leads only to their conversion to urea, or, as is a common occurrence during present parenteral nutrition therapy, hyperammonemia and hyperglycemia. Even more to the point, the prior art parenteral amino acid supplements do not lead to an increased functional capacity in muscle which is desired to decrease operative mortality and morbidity in a reasonable pre-operative period of supplementation. Unlike the feeding of livestock, which dictates so much of nutritional thinking, the increase in protein mass per se is not the goal to be sought in a human patient in need of parenteral nutrition therapy. Rather, an increased functional capacity is such a goal, and that will be judged using NMR and ergometry.

Part of the difficulty in present formulations may be due to the use of acetate in these formulations, which leads to a decrease in the phosphorylation potential, and to a severe decrease in the free [NADP$^+$]/[NADPH] ratio, in addition to the abnormalities in calcium and pyrophosphate metabolism discussed earlier. It has been suggested that the persistence of the muscle weakness and the failure of muscle mass to increase in patients receiving conventionally formulated parenteral amino acid supplements may, in fact, be a myopathy secondary to increased intracellular calcium content (see Russell D. et al. Nitrogen versus muscle calcium in the genesis of abnormal muscle function in malnutrition. *J Paren Ent Nutr* 9:415–421, 1985).

Omitted from presently available commercial mixtures, but which may optionally and advantageously be included in the new compositions of this invention, are such nitrogen containing compounds as l-carnitine, l-ornithine, l-citrulline, and the like. Carnitine, in addition to its well known role in the metabolism of fatty acids, is an important co-factor in the metabolism of the branched chain amino acids leucine, isoleucine and valine. The serum and tissue levels of l-carnitine are frequently found to be decreased in patients with malnutrition, alcoholic cirrhosis, certain congenital myopathies, and lipidemias, in patients on chronic hemodialysis, or in patients who are eating no red meat, as is the case for those receiving nutrition totally parenterally.

Hyperammonemia is a common complication of the administration of the present amino acid supplements. The urea cycle intermediates, ornithine and citrulline, may, therefore, be included with the amino acids used in an infusable fluid composition of this invention in an attempt to avoid distortion of the normal physiological levels of intermediates that exist under natural conditions. In this way, optimum function of the urea cycle is maintained during the inevitable loss of amino acids into urea which is a natural accompaniment of the ingestion of protein.

The provision of (a) a naturally balanced mixture of amino acids in concentration ratios as they exist in blood in nature, and (b) the substitution for acetate by a redox balanced mixture of anions of lactate and pyruvate and/or of anions of d-betahydroxybutyrate and acetoacetate, and/or bicarbonate and dissolved carbon dioxide in an infusion mixture, means that (1) the bone pain and abnormal calcium, phosphorus and pyrophosphate metabolism of current formulations can be avoided, (2) the absolute requirements for amino acids are decreased far below the 1 to 1.5 g nitrogen now recommended on the basis of dietary intake, (3) a more rapid increase in muscular and other organ function is achieved during parenteral fluid administration, and (4) prevention of hyperammonemia and abnormal elevations of one or another amino acids due to a functional metabolic block may be avoided.

Thus, in one aspect, the present invention provides a class of aqueous solutions adaptable for use in human parenteral nutrition therapy. A solution of this class tends (a) to normalize muscle and other organ function, (b) to maintain normal cellular phosphorylation potential, and (c) avoid acidosis and bone pain characteristic of present formulations.

As indicated above, compositions of this invention preferably contain glutamine. A glutamine-containing such composition (solution) preferably contains from about 0.03 to 120 millimoles per liter of glutamine plus at least one metabolizable nitrogen containing compound selected from among those shown in the Table 7 listing below. In Table 7 the plasma amino acids are arranged in groups, each group indicating a specified (preferred) concentration range for use in the practice of this invention. The preferred amount of each such compound in mMoles/Liter present in dissolved form in such a preferred solution of this invention is determined by a constant K which interrelates concentration ratios shown in Table 6 glutamine concentration with (other) amino acid concentration as shown by the following formula:

K=glutamine concentration/nitrogen containing compound concentration

The respective ranges for the values of K which apply for each of the four classes of amino acids shown in Table 7 appear in Table 6 below:

TABLE 6

Values for K

| Concentration Range Class | Range of K concentration ratios |
|---|---|
| I | 1.2–1.8 |
| II | 2.1–2.9 |
| III | 3.5–6.5 |
| IV | 7–19 |

The single member of Class I (that is, l-cysteine) in Table 7 is preferably added to a solution just prior to administration. The respective metabolizable nitrogen-containing compounds in each such concentration range class are as follows:

TABLE 7

Concentration Classes of Nitrogen Containing Compounds

| Class No. | Metabolizable organic nitrogen Containing Compound | Compound Reference Number |
|---|---|---|
| I | 1-Cysteine | 1 |
| II | 1-Alanine | 2 |
|  | 1-Valine | 3 |
|  | Glycine | 4 |
|  | 1-Lysine+ | 5 |
|  | 1-Proline | 6 |
| III | 1-Threonine | 7 |
|  | 1-Serine | 8 |
|  | 1-Leucine | 9 |
|  | 1-Trytophane | 10 |
|  | 1-Histidine | 11 |
|  | $NH_4^+$ | 12 |
|  | 1-Carnitine | 13 |
| IV | 1-Arginine+ | 14 |
|  | 1-Isoleucine | 15 |
|  | 1-Ornithine | 16 |
|  | 1-Glutamate- | 17 |
|  | 1-Methionine | 18 |
|  | 1-Tyrosine | 19 |
|  | 1-Phenylalanine | 20 |
|  | 1-Taurine | 21 |
|  | 1-Aspartate- | 22 |
|  | 1-Asparagine | 23 |
|  | 1-Citrulline | 24 |
|  | 1-Aminobutyrate | 25 |

In general, solutions of this invention contain nitrogen-containing positively or negatively charged metabolizable compounds which are in solution with correspondingly oppositely charged metabolites or electrolytes.

As can be seen, solutions of this invention are acetate anion free and are electrically neutral. A solution of this invention also contains at least one inorganic cation selected from the group consisting of sodium, potassium, calcium, magnesium and ammonium. The total quantity of such metabolic cation(s) present in a given solution ranges from about 0.1 to 150 mM/l. Each such dissolved metabolized organic nitrogen containing compound (including glutamine), when present in a solution of this invention, is preferably present in a concentration range extending from about 1 to 150 mM/l, although larger and smaller concentrations can be used.

EMBODIMENTS

The present invention is further illustrated by reference to the following examples. Those skilled in the art will appreciate that other and further embodiments are obvious and within the spirit and scope of this invention from the teachings of these present examples taken with the accompanying specification.

EXAMPLE A

To an aqueous solution of the hydrochloride of l-alanine is added a mole excess of dissolved l-lactic acid and the mixture is hyopholized until a solid precipitates which is the l-hydrolactate of l-alanine. Ethanol is added to promote crystallization.

Similarly, other l-lactate salts are prepared so that the following aqueous solution of l-hydrolactates of l-amino acids is formulated wherein the l-amino acid concentrations are approximately 100 times their levels in normal plasma:

| Amino Acid | mM/L |
| --- | --- |
| l-glutamine | 30.0 |
| l-cysteine | 24.0 |
| l-alanine | 14.0 |
| l-valine | 14.0 |
| glycine | 12.0 |
| l-lysine | 11.0 |
| l-proline | 11.0 |
| l-threonine | 9.0 |
| l-serine | 8.0 |
| l-leucine | 8.0 |

To this solution is added other components as in Example 1.1 to provide a composition of this invention.

EXAMPLE 1.1 AND 1.2

Examples of aqueous solutions of this invention are prepared having the following compositions:

TABLE 8

New Metabolizable Nitrogen Containing Parenteral Nutrition Solutions
Concentrations are in mMoles/L

| | Normal Plasma | Example 1.1 200 × Normal Plasma | Example 1.2 150 × Normal Plasma |
| --- | --- | --- | --- |
| l-glutamine Group I | 0.30 | 60 | 45 |
| l-cysteine Group II | 0.24 | 48 | 36 |
| l-alanine | 0.14 | 28 | 21 |
| l-valine | 0.14 | 27 | 20 |
| glycine | 0.12 | 25 | 19 |
| l-lysine$^+$ | 0.11 | 21 | 16 |
| l-proline Group III | 0.11 | 20 | 16 |
| l-threonine | 0.09 | 16 | 12 |
| l-serine | 0.08 | 16 | 12 |
| l-leucine | 0.08 | 15 | 11 |
| l-tryptophine | 0.05 | 11 | 8 |
| l-histidine | 0.05 | 10 | 8 |
| $NH_4^+$ | 0.05 | — | — |
| l-carnitine Group IV | 0.05 | 9 | 7 |
| l-arginine$^+$ | 0.04 | 8 | 6 |
| l-isoleucine | 0.04 | 7 | 5 |
| l-ornithine | 0.03 | 7 | 5 |
| l-glutamate$^-$ | 0.03 | 6 | 5 |
| l-methionine | 0.03 | 6 | 4 |
| l-tyrosine | 0.03 | 6 | 4 |

TABLE 8-continued

New Metabolizable Nitrogen Containing Parenteral Nutrition Solutions
Concentrations are in mMoles/L

| | Normal Plasma | Example 1.1 200 × Normal Plasma | Example 1.2 150 × Normal Plasma |
| --- | --- | --- | --- |
| l-phenylalanine | 0.03 | 6 | 4 |
| l-taurine | 0.02 | — | — |
| l-aspartate$^-$ | 0.02 | 4 | 3 |
| l-asparagine | 0.02 | 4 | 3 |
| l-citrulline | 0.02 | — | 3 |
| l-aminobutyrate | 0.02 | — | — |
| $K^+$ | 5 | 10 | 8 |
| l-lactate$^+$ | 1–6 | 26 | 20 |
| pyruvate$^-$ | | 3 | 2 |
| mMole/L | 311 | 403 | 303 |

EXAMPLES 1.3–1.5

Further examples of aqueous solutions of this invention are prepared having the following components:

TABLE 9

New Metabolizable Nitrogen Containing Parenteral Nutrition Solutions
Concentrations are in mMoles/L.

| | Example 1.3 200 × Normal | Example 1.4 200 × Normal | Example 1.5 200 × Normal |
| --- | --- | --- | --- |
| l-glutamine Group I | 60 | 60 | 60 |
| l-cysteine Group II | 48 | 48 | 48 |
| l-alanine | 28 | 28 | 28 |
| l-valine | 27 | 27 | 27 |
| glycine | 25 | 25 | 25 |
| l-lysine$^+$ | 21 | 21 | 21 |
| l-proline Group III | 20 | 20 | 20 |
| l-threonine | 16 | 16 | 16 |
| l-serine | 16 | 16 | 16 |
| l-leucine | 15 | 15 | 15 |
| l-tryptophine | 11 | 11 | 11 |
| l-histidine | 10 | 10 | 10 |
| $NH_4^+$ | — | — | — |
| l-carnitine Group IV | 9 | 9 | 9 |
| l-arginine$^+$ | 8 | 8 | 8 |
| l-isoleucine | 7 | 7 | 7 |
| l-ornithine | 7 | 7 | 7 |
| l-glutamate$^-$ | 6 | 6 | 6 |
| l-methionine | 6 | 6 | 6 |
| l-tyrosine | 6 | 6 | 6 |
| l-phenylalanine | 6 | 6 | 6 |
| l-taurine | — | — | — |
| l-aspartate$^-$ | 4 | 4 | 4 |
| l-asparagine | 4 | 4 | 4 |
| l-citrulline | — | — | — |
| l-aminobutyrate | — | — | — |
| $Na^+$ | 10 | 12.5 | 12.5 |
| l-lactate$^-$ | 54 | 53 | 54 |
| alphaketoglutarate$^{2-}$ | | 1.2 | 1.2 |
| $NH_4^+$ | | | 1 |
| mMole/L | 425 | 427 | 428 |

EXAMPLE 2

The route of administration has an effect upon maximum dosage of nitrogen containing compounds and caloric supplementation.

Parenteral nutrition is now characteristically given, either through normal intravenous lines, using only slightly hyperosmolar solutions, or through grossly hypertonic solutions administered through indwelling catheters placed in a deep vein. Both are unphysiologic in that the bulk of the nutrients normally provided to the body enter through the portal vein, where very large concentrations of substrates normally occur in a postprandial state (Veech R L, unpublished data).

After recovery from the implantation of a cannula in a deep vein each of the formulations Examples 1.1 and 1.2 at the dose rate of 2 ml are administered to three starved Sprague Dawley male rats over one hour in combination with 3 ml of 5% dextrose in water. The effects on the plasma and tissue metabolite levels and rate of protein turnover are measured following established methods, such as those described by Poso and Mortemore, 1984. In chronic experiments, change in lean body and bone mass is measured. Exercise tolerance and $^{31}$NMR of their muscles at rest, and during exercise, is measured, and the animals are sacrificed. The accumulation of pyrophosphate, phosphate, calcium, and other relevant electrolytes and metabolic intermediates is determined in blood, liver and skeletal muscle after freeze clamping of these organs during administration of the two different parenteral nutrition formulations. In addition, the total protein content of liver and skeletal muscle on the two types of formulations is determined as is the liver, muscle and blood content of amino acids, soluble CoA's, phosphorylation potential or [ATP]/[ADP][Pi] ratio, the redox state of the free pyridine nucleotide couples or [NAD(P)$^+$]/[NAD(P)H] ratios using the two formulations. The $^{31}$p NMR determinations are performed upon the rat hind limb placed in a NMR tube and pulsed by electrical stimulation. It is found that the function of skeletal muscle with the new formulations is approximately normal.

Other and further aims, objects, purposes, advantages, uses, and the like for the present invention will be apparent to those skilled in the art from the present specification. The problems in acetate administration, including pyrophosphate and calcium build-up in liver, post-dialysis hyperphosphatemia and hyperparathyroidism are avoided. Likewise, the abnormal redox state with diminished [ATP]/[ADP][Pi] ratio seen with acetate alone may be eliminated.

I claim:

1. A non-hyperchloremic, alkalinizing aqueous solution for parenteral nutrition comprising water having dissolved therein:

(A) from about 1 to 150 mMoles/L of at least one of the following metabolizable nitrogen containing compounds:

l-glutamine
l-cysteine
l-alanine
l-valine
glycine
l-lysine$^+$
l-proline
l-threonine
l-serine
l-leucine
l-tryptophane
l-histidine
ammonium$^+$
l-carnitine
l-arginine$^+$
l-isoleucine
l-ornithine
l-glutamate$^-$
l-methionine
l-tyrosine
l-phenylalanine
l-aspartate$^-$
l-asparagine
l-citrulline but always containing l-glutamine the total quantity of all such compound(s) in any given such solution being not more than about 1000 mMoles/Liter, (B) from about 0.1 to 150 mMoles/Liter of at least one carboxylate anion selected from the group consisting of l-lactate with substantially no d-lactate, pyruvate, d-betahydroxybutyrate, acetoacetate, alpha Ketoglutarate l-glutamate, and bicarbonate, and (C) from about 0.1 to 150 mMoles/Liter of at least one cation selected from the group consisting of sodium, potassium, calcium, magnesium, and ammonium.

2. The solution of claim 1 wherein there is dissolved at least one osmotically active nonionic water soluble nutrient in a total quantity ranging from about 5 to 400 mMoles per liter.

3. The solution of claim 1 wherein said anions are employed as pairs and such pairs are selected from the group consisting of from about 1 to 150 mMoles/Liter total of (A) l-lactate anions and pyruvate anions in a milliequivalent ratio ranging from about 1:1 to 20:1, (B) from about 1 to 150 mMoles/Liter total of d-betahydroxybutyrate anions and acetoacetate anions in a milliequivalent ratio ranging from about 0.5:1 to 6:1, (C) from about 1 to 150 mMoles/Liter total of bicarbonate anions and dissolved carbon dioxide in a milliequivalent ratio ranging from about 1:1 to 100:1, there being at least one such pair in said solution.

4. The solution of claim 1 wherein said nitrogen containing compounds include at least one material selected from the group consisting of alanine, glutamine, glutamate, wherein said carboxylate anions include at least one selected from the group consisting of l-lactate and alpha ketoglutarate, and wherein:

(A) from 1 to 150 mMoles/Liter total of l-lactate anions and alanine are present in a ratio in moles per liter of l-lactate anions to alanine ranges from about 0.5:1 to 20:1, (B) from 1 to 150 mMoles/Liter total of glutamine and alpha ketoglutarate anions are present, the ratio in moles per liter of glutamine to alphaketoglutarate anions ranges from about 1:1 to 50:1, and (C) from about 1 to 150 mMoles/Liter total of when ammonium and glutamate and alpha ketoglutarate anions are present, the ratio in moles/liter of [glutamate$^-$] to the product of moles/liter ammonium$^+$ times moles/liter of alpha ketoglutarate$^{2-}$ ranges from about 1000 to 100,000 Moles/Liter.

5. An aqueous solution adaptable for use in human parenteral nutrition therapy and which solution tends (a) to normalize muscle and other organ function and (b) to maintain normal cellular phosphorylation potential, said solution comprising from about 0.03 to 120 millimoles per liter of glutamine plus at least five metabolizable nitrogen containing compounds selected from among the following compounds:

| Class No. | Metabolizing Nitrogen Containing Compound |
|---|---|
| I | 1-Cysteine |
| II | 1-Alanine |
|  | 1-Valine |
|  | Glycine |
|  | 1-Lysine$^+$ |
|  | 1-Proline |
| III | 1-Threonine |
|  | 1-Serine |
|  | 1-Leucine |
|  | 1-Tryptophane |
|  | 1-Histidine |
|  | ammonium$^+$ |
|  | 1-Carnitine |
| IV | 1-Arginine |
|  | 1-Isoleucine |
|  | 1-Ornithine |
|  | 1-Glutamate$^-$ |
|  | 1-Methionine |
|  | 1-Tyrosine |
|  | 1-Phenylalanine |
|  | 1-Taurine |
|  | 1-Aspartate |
|  | 1-Asparagine |
|  | 1-Citrulline |
|  | 1-Aminobutyrate | the concentration range of each such compound in millimoles per liter being determined by the following formula:

$$\text{nitrogen containing compound concentration} = \frac{\text{glutamine concentration}}{K}$$

where the glutamine concentration is in millimoles per liter and the value of K for each given such nitrogen containing compound is determined by its particular Class above indicated which is associated with such compound in accordance with the following table:

| Class | Range of values for K |
|---|---|
| I | 1.2–1.8 |
| II | 2.1–2.9 |
| III | 3.5–6.5 |
| IV | 7–19 |

6. A solution of claim 5 additionally containing at least one cation selected from the group consisting of sodium$^+$, potassium$^+$, magnesium$^{2+}$, calcium$^+$, ammonium$^+$ and at least one anion selected from the group consisting of 1-lactate$^-$ with substantially no d-lactate, pyruvate$^-$, d-betahydroxybutyrate$^-$, acetoacetate$^-$, and alphaketoglutarate$^{2-}$, such ions being present in a total amount ranging from about 0.1 to 120 mM/l.

7. The solution of claim 5 wherein the respective amounts of said anions are such as to define near equilibrium couples of
   (A) 1-lactate with substantially no d-lactate and pyruvate in a molar concentration ratio ranging from about 20:1 to 1:1 1-lactate to pyruvate, and
   (B) d-betahydroxybutyrate and acetoacetate in a molar concentration ratio ranging from about 6:1 to 0.5:1 d-betahydroxybutyrate to acetoacetate.

8. An in vivo process for accomplishing parenteral nutrition which comprises introducing intravenously a composition of claim 5 into a mammal at a rate which is at least sufficient to normalize organ function and phosphorylation potential.

9. The solution of claim 5 comprising at least ten of said metabolizable nitrogen containing compounds.

10. The solution of claim 5 comprising all of said metabolizable nitrogen containing compounds.

11. A method for controlling the redox state and the phosphorylation potential during parenteral fluid therapy comprising intravenously administering to a human patient a solution of claim 4.

12. A compound comprising a salt of at least one metabolizable acid selected from the group consisting of 1-lactic acid with substantially no d-lactic acid, pyruvic acid, d-betahydroxybutyric acid, acetoacetic acid and alphaketoglutaric acid with at least one metabolizable nitrogen containing compound selected from the group consisting of l-glutamine
l-cysteine
l-alanine
l-valine
glycine
l-lysine$^+$
l-proline
l-threonine
l-serine
l-leucine
l-tryptophane
l-histidine
ammonium$^+$
l-carnitine
l-arginine$^+$
l-isoleucine
l-ornithine
l-glutamate$^-$
l-methionine
l-tyrosine
l-phenylalanine
l-aspartate$^-$
l-asparagine
l-citrulline.

13. A solution comprising water having dissolved therein:
   (A) from about 1 to 150 mMoles/L of at least one of the following metabolizable nitrogen containing compounds:

l-glutamine
l-cysteine
l-alanine
l-valine
glycine
l-lysine$^+$
l-proline
l-threonine
l-serine
l-leucine
l-tryptophane
l-histidine
ammonium$^+$
l-carmotome
l-arginine$^+$
l-isoleucine
l-ornithine l-glutamate
l-methionine
l-tyrosine
l-phenylalanine
l-aspartate⁻
l-asparagine
l-citrulline but always containing l-glutamine the total quantity of all such compound(s) in any given such solution being not more than about 1000 mMoles/Liter, (B) from about 0.1 to 150 mMoles/Liter of at least one carboxylate anion selected from the group consisting of l-lactate with substantially no d-lactate, pyruvate: d-betahydroxybutyrate, acetoacetate, l-glutamate, and bicarbonate, and (C) from about 0.1 to 150 mMoles/Liter of at least one cation selected from the group consisting of sodium, potassium, calcium, magnesium, and ammonium.

14. A solution comprising water having dissolved therein:

(A) from about 1 to 150 mMoles/L of at least one of the following metabolizable nitrogen containing compounds:

l-glutamine
l-cysteine
l-alanine
glycine
l-lysine⁺
l-proline
l-threonine
l-serine
l-leucine
l-tryptophane
l-histidine
ammonium⁺
l-carmotome
l-arginine+
l-isoleucine
l-ornithine
l-glutamate⁻
l-methionine
l-tyrosine
l-phenylalanine
l-aspartate⁻
l-asparagine
l-citrulline but always containing L-glutamine the total quantity of all such compound(s) in any given such solution being not more than about 1000 mMoles/Liter, (B) from about 0.1 to 150 mMoles/Liter of at least one carboxylate anion selected from the group consisting of l-lactate with substantially no d-lactate, pyruvate, d-betahydroxybutyrate, acetoacetate, l-glutamate, and bicarbonate, and (C) from about 0.1 to 150 mMoles/Liter of at least one cation selected from the group consisting of sodium, potassium, calcium, magnesium, and ammonium, wherein said nitrogen containing compounds include at least one material selected from the group consisting of alanine, glutamine, glutamate, wherein said carboxylate anions include at least one selected from the group consisting of l-lactate and alpha ketoglutarate, and wherein:

(A) from 1 to 150 mMoles/Liter total of l-lactate anions and alanine are present in a ratio in moles per liter of l-lactate anions to alanine ranges from about 0.5:1 to 20:1, (B) from 1 to 150 mMoles/Liter total of glutamine and alpha ketoglutarate anions are present, the ratio in moles per liter of glutamine to alphaketoglutarate anions ranges from about 1:1 to 50:1, and (C) from about 1 to 150 mMoles/Liter total of when ammonium and glutamate and alpha ketoglutarate anions are present, the ratio in moles/liter of glutamate− to the product of moles/liter ammonium⁺ times moles/liter of alpha ketoglutarate$^{2-}$ ranges from about 1000 to 100,000 Moles/Liter.

* * * * *

UNITED STATES PATENT AND TRADEMARK OFFICE
CERTIFICATE OF CORRECTION

| | | |
|---|---|---|
| PATENT NO. | : 5,719,119 | Page 1 of 1 |
| APPLICATION NO. | : 08/053291 | |
| DATED | : February 17, 1998 | |
| INVENTOR(S) | : Richard L. Veech | |

It is certified that error appears in the above-identified patent and that said Letters Patent is hereby corrected as shown below:

<u>COLUMN 24</u>

Line 9, change "compound" to --composition--.

Signed and Sealed this

Eighth Day of July, 2008

JON W. DUDAS
*Director of the United States Patent and Trademark Office*

(12) EX PARTE REEXAMINATION CERTIFICATE (8801st)
United States Patent
Veech

(10) Patent Number: US 5,719,119 C1
(45) Certificate Issued: Jan. 17, 2012

(54) PARENTERAL NUTRITION THERAPY WITH AMINO ACIDS

(75) Inventor: Richard L. Veech, Rockville, MD (US)

(73) Assignee: Multi Formulations Ltd., Oakville (CA)

Reexamination Request:
No. 90/009,545, Jul. 29, 2009

Reexamination Certificate for:
Patent No.: 5,719,119
Issued: Feb. 17, 1998
Appl. No.: 08/053,291
Filed: Apr. 26, 1993

Certificate of Correction issued Jul. 8, 2008.

Related U.S. Application Data

(63) Continuation of application No. 07/782,751, filed on Oct. 21, 1991, now abandoned, which is a continuation of application No. 07/479,237, filed on Feb. 12, 1990, now abandoned, which is a continuation of application No. 06/940,332, filed on Dec. 17, 1986, now abandoned, which is a continuation-in-part of application No. 06/810,916, filed on Dec. 18, 1985, now abandoned.

(51) Int. Cl.
*A61K 33/10* (2006.01)
*A61K 33/06* (2006.01)

(52) U.S. Cl. .......... 514/5.5; 424/601; 424/633; 424/677; 424/678; 424/679; 424/680; 424/719; 514/15.1; 514/546; 514/557; 514/561; 514/578

(58) Field of Classification Search .............. None
See application file for complete search history.

(56) References Cited

To view the complete listing of prior art documents cited during the proceeding for Reexamination Control Number 90/009,545, please refer to the USPTO's public Patent Application Information Retrieval (PAIR) system under the Display References tab.

*Primary Examiner* — Gary Kunz

(57) ABSTRACT

Parenteral nutrition aqueous solutions are provided which preferably contain glutamine together with other organic nitrogen containing compounds. The respective concentrations of the compounds present in any given such solution are typically approximately multiples of the concentration of the same compounds as found in normal human plasma, and the respective mole ratios of various such compounds in any given such solution relative to one another are approximately the same mole ratio associated with the same compounds as found in normal human plasma. Processes for using such solutions are provided.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 12 is determined to be patentable as amended.

New claims 15-17 are added and determined to be patentable.

Claims 1-11, 13 and 14 were not reexamined.

12. A *nutritional supplement* composition comprising*:*
(a) a salt of [at least one metabolizable acid selected from the group consisting of l-lactic acid with substantially no d-lactic acid, pyruvic acid, d-betahydroxybutyric acid, acetoacetic acid and] alphaketoglutaric acid*;*
(b) [with] at least one metabolizable nitrogen containing compound selected from the group consisting of
[l-glutamine]
l-cysteine
l-alanine
l-valine
glycine
l-lysine$^+$
l-proline
l-threonine
l-serine
l-leucine
l-tryptophane
l-histidine
ammonium$^+$
l-carnitine
l-arginine$^+$
l-isoleucine
l-ornithine
l-glutamate$^-$
l-methionine
l-tyrosine
l-phenylalanine
*l-taurine*
l-aspartate$^-$
l-asparagine
l-citrulline
*l-aminobutyrate; and*
*(c) l-glutamine;*
*(d) wherein component amounts and relationships of component amounts are established such that the ratio of l-glutamine to alpha ketoglutaric acid is within the range of 2:1 to 50:1; and*
*(e) compounds in the composition are present at concentrations that are at least a multiple of physiologic concentrations of such compounds found in normal human plasma.*

*15. The nutritional supplement composition of claim 12 wherein the multiple of physiologic concentrations is 100 times.*

*16. The nutritional supplement composition of claim 12 wherein the multiple of physiologic concentrations is 150 times.*

*17. The nutritional supplement composition of claim 12 wherein the multiple of physiologic concentrations is 200 times.*

\* \* \* \* \*